United States Patent
Richardson

(10) Patent No.: US 10,014,198 B2
(45) Date of Patent: Jul. 3, 2018

(54) WEAR DETECTION OF CONSUMABLE PART IN SEMICONDUCTOR MANUFACTURING EQUIPMENT

(71) Applicant: Lam Research Corporation, Fremont, CA (US)

(72) Inventor: Brett C. Richardson, San Ramon, CA (US)

(73) Assignee: Lam Research Corporation, Fremont, CA (US)

( * ) Notice: Subject to any disclaimer, the term of this patent is extended or adjusted under 35 U.S.C. 154(b) by 322 days.

(21) Appl. No.: 14/846,635

(22) Filed: Sep. 4, 2015

(65) Prior Publication Data

US 2017/0053819 A1    Feb. 23, 2017

Related U.S. Application Data

(60) Provisional application No. 62/208,499, filed on Aug. 21, 2015.

(51) Int. Cl.

| | |
|---|---|
| *H01L 21/66* | (2006.01) |
| *H01L 23/58* | (2006.01) |
| *G01N 21/88* | (2006.01) |
| *G01N 21/95* | (2006.01) |
| *H01L 21/67* | (2006.01) |
| *H01J 37/32* | (2006.01) |
| *H01L 21/677* | (2006.01) |

(52) U.S. Cl.
CPC ....... *H01L 21/67288* (2013.01); *G01N 21/88* (2013.01); *G01N 21/9501* (2013.01); *H01J 37/32009* (2013.01); *H01J 37/3244* (2013.01); *H01L 21/67253* (2013.01); *H01L 21/67259* (2013.01); *H01L 21/67742* (2013.01); *H01L 21/67748* (2013.01); *H01J 2237/332* (2013.01); *H01J 2237/334* (2013.01)

(58) Field of Classification Search
CPC ...... G01N 3/56; G01N 21/9501; G01N 21/88; H01L 21/67253; H01L 21/67288; H01L 21/67748; H01J 37/3244; H01J 37/32009; H01J 21/67259; H01L 21/67742; H01J 2237/332; H01J 2237/334
See application file for complete search history.

(56) References Cited

U.S. PATENT DOCUMENTS

| | | | |
|---|---|---|---|
| 8,730,482 B2 * | 5/2014 | Matsudo | G01B 11/06 356/479 |
| 2006/0157698 A1 * | 7/2006 | Miyajima | H01L 21/67288 257/48 |

* cited by examiner

*Primary Examiner* — Hina F Ayub
*Assistant Examiner* — Amanda Merlino
(74) *Attorney, Agent, or Firm* — Martine Penilla Group, LLP

(57) ABSTRACT

Methods, systems, and computer programs are presented for determining wear of a consumable part in a semiconductor processing apparatus. One chamber includes a reference part, a consumable part, a transfer arm for transferring the substrate into the chamber, a sensor on the transfer arm, and a controller. The reference part is not subject to wear during operation of the chamber, while the consumable part is subject to wear. The sensor is configured to measure a first distance from the sensor to a surface of the consumable part as the transfer arm travels near the consumable part, and the sensor is configured to measure a second distance from the sensor to a surface of the reference part as the transfer arm travels near the reference part. The controller determines the wear amount of the consumable part based on the first distance and the second distance.

20 Claims, 8 Drawing Sheets

WEAR DETECTION OF CONSUMABLE PART IN SEMICONDUCTOR MANUFACTURING EQUIPMENT

CLAIM OF PRIORITY

This application claims priority from U.S. Provisional Patent Application No. 62/208,499, filed Aug. 21, 2015, and entitled "WEAR DETECTION OF CONSUMABLE PART IN SEMICONDUCTOR MANUFACTURING EQUIPMENT." This provisional application is herein incorporated by reference.

BACKGROUND

1. Field of the Invention

The present embodiments relates to methods, systems, and programs for detecting wear of a consumable part in semiconductor manufacturing equipment.

2. Description of the Related Art

Plasma has long been employed to process substrates (e.g., wafers or flat panels) to form electronic products (e.g., integrated circuits or flat panel displays). Semiconductor wafers are typically placed in an etch chamber with a photoresist mask layer to direct the etch of the underlying materials. The etching process removes the underlying materials not covered by the photoresist.

Etch systems have consumable parts in the chamber that wear off during the operation of the chamber. This requires periodic replacement of the consumable parts to maintain the on-wafer process performance according to specification, including CD (Critical Dimension) control, etch uniformity and defectivity. In a production environment, a single etch chamber may be used for multiple etch processes, each potentially having a different impact on the wear rate of chamber consumable parts. This makes it difficult to predict when a part will wear out and require maintenance, and if there is a known process adjustment available to compensate for wear, it may be difficult to know when to make adjustments in real time.

Some system administrators base consumable part replacement on the number of chamber processing hours, number of wafers run, or out-of-specification wafer metrology data. However, time-based maintenance schedules may lead to premature replacement of chamber parts, as the system has to account for the worst-case process condition. Further, wafer-metrology-based maintenance or process adjustments may suffer from a delay in feedback response of several hours or several days, until post-etch metrology tests are completed, which exposes wafers to risk while the process fault is detected.

It is in this context that embodiments arise.

SUMMARY

Methods, devices, systems, and computer programs are presented for determining wear of a consumable part in a semiconductor processing apparatus. It should be appreciated that the present embodiments can be implemented in numerous ways, such as a method, an apparatus, a system, a device, or a computer program on a computer readable medium. Several embodiments are described below.

A system of one or more computers can be configured to perform particular operations or actions by virtue of having software, firmware, hardware, or a combination of them installed on the system that in operation cause the system to perform the actions. One or more computer programs can be configured to perform particular operations by virtue of including instructions that, when executed by data processing apparatus, cause the apparatus to perform the actions. One general aspect includes a chamber for processing a substrate, the chamber including a reference part, a consumable part, a transfer arm, a sensor, and a controller. The reference part is not subject to wear during operation of the chamber, while the consumable part is subject to wear during operation of the chamber. The transfer arm is for transferring the substrate into the chamber, and the sensor is configured to measure a first distance from the sensor to a surface of the consumable part as the transfer arm travels near the consumable part. Further, the sensor is configured to measure a second distance from the sensor to a surface of the reference part as the transfer arm travels near the reference part. The controller is configured to determine a wear amount of the consumable part based on the first distance and the second distance. Other embodiments of this aspect include corresponding computer systems, and computer programs recorded on one or more computer storage devices, each configured to perform the actions of the methods.

Implementations may include one or more of the following features. The chamber as recited where the controller calculates a distance difference between a plane of the surface of the consumable part and a plane of the surface of the reference part, the distance difference being equal to the first distance minus the second distance. The chamber as recited where the controller tracks a change of the distance difference over time starting when the consumable part is first installed. The chamber as recited where the controller determines that the consumable part is to be replaced when the distance difference changes by a predetermined amount in reference to the distance difference measured when the consumable part was first installed. The chamber as recited where the wear amount on the consumable part is determined without having to open the chamber, where the sensor is a non-contact distant measurement device. The chamber as recited where the controller calculates a distance difference between a plane of the surface of the consumable part and a plane of the surface of the reference part, the distance difference being equal to the first distance minus the second distance, where the controller determines a process parameter change to compensate for wear of the consumable part based on the change of the distance difference over time starting when the consumable part is first installed. The chamber as recited where the sensor is coupled to an end effector of the transfer arm. The chamber as recited where the sensor is one of a depth camera, or a confocal chromatic measurement device, or a low coherence interferometry measurement device, or a capacitance distance sensor, or a color change detector. The chamber as recited further including a station in the vacuum transfer chamber or a load lock for storing the sensor, where the transfer arm loads the sensor from the station in the vacuum transfer chamber or load lock. The chamber as recited where the consumable part is an edge ring, where the reference part is a chuck for holding the substrate during operation of the chamber. The chamber as recited where the sensor is connected wirelessly to the controller, where the sensor includes a battery. The chamber as recited where the sensor is mountable on an end effector of the transfer arm. The chamber as recited where the sensor is mounted on a structure similar to a substrate such that the transfer arm loads the sensor as if the transfer arm were loading a substrate.

One general aspect includes a method for determining wear of a consumable part, the method including an operation for loading a substrate on a transfer arm in a semiconductor manufacturing chamber, the transfer arm including a sensor. The method also includes an operation for measuring, with the sensor, a first distance from the sensor to a surface of a consumable part as the transfer arm travels near the consumable part, the consumable part being subject to wear during operation of the chamber. The method also includes an operation for measuring, with the sensor, a second distance from the sensor to a surface of a reference part as the transfer arm travels near the reference part, the reference part not being subject to wear during operation of the chamber. The method also includes an operation for determining a wear amount of the consumable part based on the first distance and the second distance.

One general aspect includes a chamber for processing a substrate, the chamber including a reference part, a consumable part, a transfer arm, a sensor, and a controller. The consumable part accumulates deposition during operation of the chamber. Further, the transfer arm is for transferring the substrate into the chamber. The sensor is on the transfer arm, where the sensor is configured to measure a first distance from the sensor to a surface of the consumable part as the transfer arm travels near the consumable part, where the sensor is configured to measure a second distance from the sensor to a surface of the reference part as the transfer arm travels near the reference part. The controller is configured to determine an amount of deposition on the consumable part based on the first distance and the second distance. Other embodiments of this aspect include corresponding computer systems, apparatus, and computer programs recorded on one or more computer storage devices, each configured to perform the actions of the methods.

Other aspects will become apparent from the following detailed description, taken in conjunction with the accompanying drawings.

BRIEF DESCRIPTION OF THE DRAWINGS

The embodiments may best be understood by reference to the following description taken in conjunction with the accompanying drawings.

DETAILED DESCRIPTION

One chamber includes a chuck for holding a substrate during processing, an edge ring configured to surround the substrate during processing, a transfer arm for transferring the substrate to the chuck, a distance sensor on the transfer arm, and a controller. The distance sensor is configured to measure a first distance from the distance sensor to a top surface of the edge ring as the transfer arm travels over the edge ring, and the distance sensor is also configured to measure a second distance from the distance sensor to a top surface of the chuck as the transfer arm travels over the chuck. The controller is configured to determine a wear amount of the edge ring based on the first distance and the second distance, because the difference between the first distance and the second distance is an indicator of the amount of wear of the edge ring. When the wear amount exceeds a predetermined threshold, it is time to replace the edge ring.

Embodiments present methods to measure the wear rate and profile of consumable parts in the etch chamber, in-situ, and using non-contact surface profilometry (e.g., confocal chromatic measurement, low coherence interferometry, or capacitance distance sensors). The distance sensor is placed on the transfer arm, or in a separate probe arm, and is periodically inserted into the chamber through the wafer transfer door. The wear profile of the part of interest is generated by mapping the distance from the distance sensor to the consumable part over time.

It will be apparent, that the present embodiments may be practiced without some or all of these specific details. In other instances, well-known process operations have not been described in detail in order not to unnecessarily obscure the present embodiments.

Figure 1:
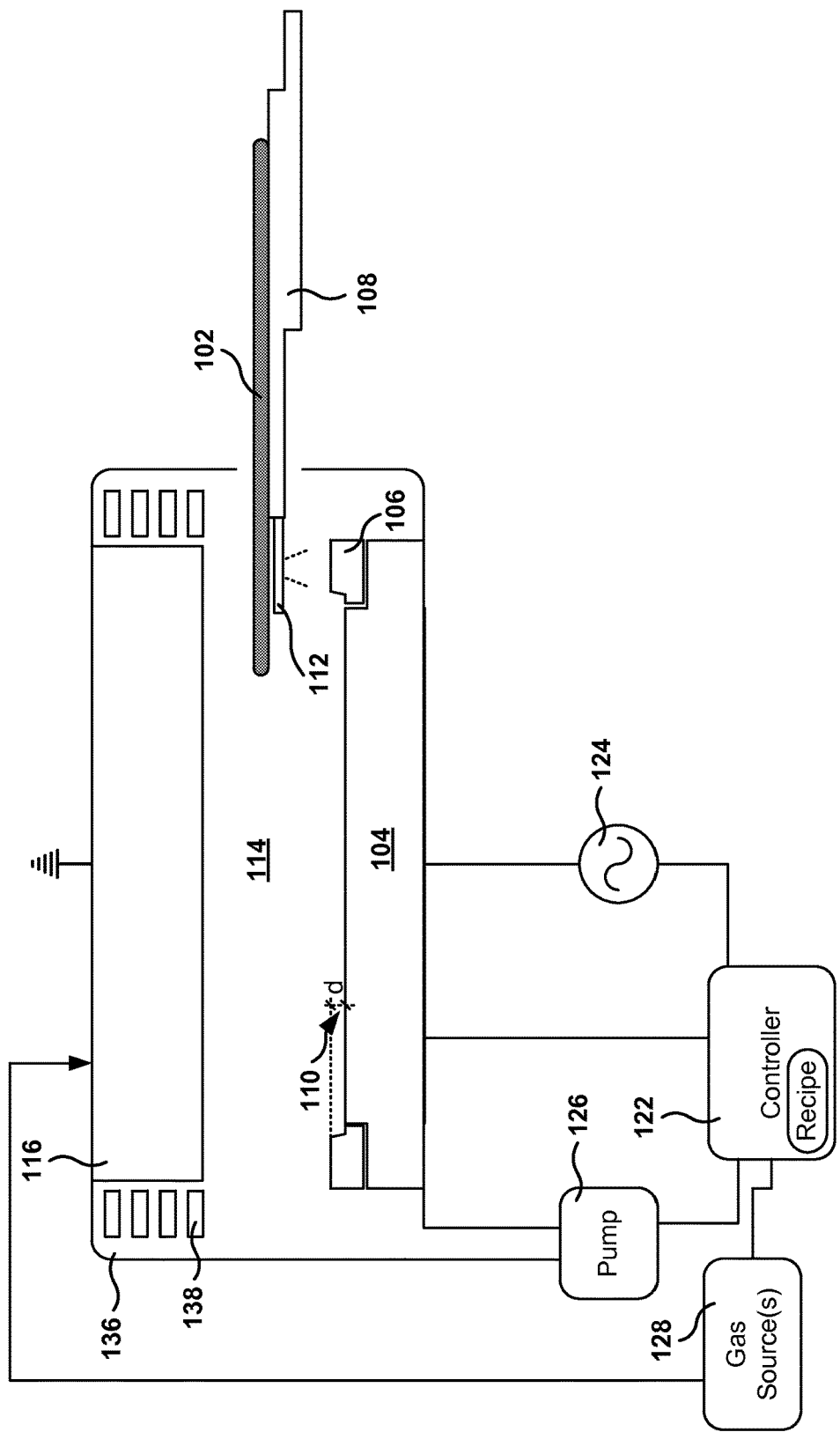
FIG. 1 illustrates the loading of a wafer in a capacitive coupled plasma processing system, according to one embodiment.

FIG. 1 illustrates the loading of a wafer in a capacitive coupled plasma processing system, according to one embodiment. The capacitive coupled plasma processing system includes a chamber 114 for processing plasma, controller 122, radiofrequency (RF) source 124, pump 126, and one or more gas sources 128. In some embodiments, the chamber may have one or more RF sources coupled to the top electrode. The chamber 114 includes chuck 104 (e.g., electrostatic chuck) for supporting a substrate 102, also referred to as a wafer, to be processed, and an edge ring 106. In some embodiments, the chamber 114 may also include confinement rings 138 for confining the plasma in the chamber, and a chamber wall cover 136.

FIG. 1 illustrates a substrate 102 being transferred into the chamber by transfer arm 108. During transfer, confinement rings 138 are moved upward in order to allow the transfer arm to enter into the chamber 114 through a slot on the side of the chamber. During operation of the chamber, confinement rings 138 are lowered so confinement rings 138 cover the chamber wall cover 136 to avoid contact with the plasma.

In one embodiment, transfer arm 108 includes a distance sensor 112 for measuring the distance from the distance sensor 112 to a remote surface without having to contact the remote surface. In other words, the distance sensor is able to measure the distance to the remote surface using an optical, acoustic, or radio device.

Some of the parts inside the chamber are consumable parts, which, due to the impact of etching or other processes in the chamber, have to be replaced after a certain number of hours of operation because of the degradation of the parts. For example, edge ring 106, confinement rings 138, chamber wall cover 136, are examples of consumable parts, but other chambers may include additional parts that are also consumable and need to be replaced over time. Embodiments presented herein are described with reference to measuring the wear on the edge ring 106, but the principles presented may be utilized to measure the wear on any other consumable part within the chamber.

In one embodiment, a distance d 110 is defined as the vertical distance between the top surface of the edge ring 106 and the top surface of the chuck 104, i.e., the distance d 110 is measured as the vertical distance between the planes defined by the top surface of the edge ring 106 and the top surface of the chuck 104. In general, the distance d changes over time due to the wear of the edge ring, since the top surface of the chuck 104 does not typically change, as the chuck is covered by the substrate 102 during the operation of the chamber.

RF source 124 can include multiple RF sources or a single RF source capable of producing multiple frequencies of the RF signals from between about 100 kHz to about 300 MHz. By way of example, some RF signals have frequencies of about 27 MHz to about 60 MHz. The RF signals can have an RF power of between about 50 w and about 10 Kw. By way of example, between about 100 w and about 1500 w. The RF source 124 can produce pulsed or non-pulsed RF signals.

The controller 122 includes a processor, memory, software logic, hardware logic and input and output subsystems for communicating with, monitoring and controlling the plasma processing system. The controller 122 also includes one or more recipes including multiple set points for various operating parameters (e.g., voltage, current, frequency, pressure, flow rate, power, temperature, etc.) for operating the plasma processing system. In one embodiment, controller 122 is configured to determine the wear on a consumable part based on distance parameters obtain by the distance sensor 112. By comparing the distance measurements taken over time, the controller is able to determine wear on the part. For example, an increase distance measured to the edge ring 106 will mean that the edge ring 106 is wearing off on the top. Therefore, when the wear on the edge ring 106 exceeds a predetermined threshold, the controller will set up an alert to replace the edge ring 106.

The chamber 114 also includes an upper electrode 116. In operation, the upper electrode 116 is typically grounded but could be biased or coupled to a second RF source (not shown). The RF source 124 provides an RF signal to the chuck 104 and the gas sources 128 inject the desired process gas/es into the chamber 114. A plasma 120 is then formed between the upper electrode 116 and the chuck 104. The plasma 120 can be used to etch the surface of the substrate 102 or volatilize deposits formed on various inner surfaces of the chamber 114.

In some implementations, a controller is part of a system, which may be part of the above-described examples. Such systems can comprise semiconductor processing equipment, including a processing tool or tools, chamber or chambers, a platform or platforms for processing, and/or specific processing components (a wafer pedestal, a gas flow system, etc.). These systems may be integrated with electronics for controlling their operation before, during, and after processing of a semiconductor wafer or substrate. The electronics may be referred to as the "controller," which may control various components or subparts of the system or systems. The controller, depending on the processing requirements and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, wafer transfers into and out of a tool and other transfer tools and/or load locks connected to or interfaced with a specific system.

Broadly speaking, the controller may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor wafer or to a system. The operational parameters may, in some embodiments, be part of a recipe defined by process engineers to accomplish one or more processing steps during the fabrication of one or more layers, materials, metals, oxides, silicon, silicon dioxide, surfaces, circuits, and/or dies of a wafer.

The controller, in some implementations, may be a part of or coupled to a computer that is integrated with, coupled to the system, otherwise networked to the system, or a combination thereof. For example, the controller may be in the "cloud" or all or a part of a fab host computer system, which can allow for remote access of the wafer processing. The computer may enable remote access to the system to monitor current progress of fabrication operations, examine a history of past fabrication operations, examine trends or performance metrics from a plurality of fabrication operations, to change parameters of current processing, to set processing steps to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

Without limitation, example systems may include a plasma etch chamber or module, a deposition chamber or module, a spin-rinse chamber or module, a metal plating chamber or module, a clean chamber or module, a bevel edge etch chamber or module, a physical vapor deposition (PVD) chamber or module, a chemical vapor deposition (CVD) chamber or module, an atomic layer deposition (ALD) chamber or module, an atomic layer etch (ALE) chamber or module, an ion implantation chamber or module, a track chamber or module, and any other semiconductor processing systems that may be associated or used in the fabrication and/or manufacturing of semiconductor wafers.

As noted above, depending on the process step or steps to be performed by the tool, the controller might communicate with one or more of other tool circuits or modules, other tool components, cluster tools, other tool interfaces, adjacent tools, neighboring tools, tools located throughout a factory, a main computer, another controller, or tools used in material transport that bring containers of wafers to and from tool locations and/or load ports in a semiconductor manufacturing factory.

Figure 2A:
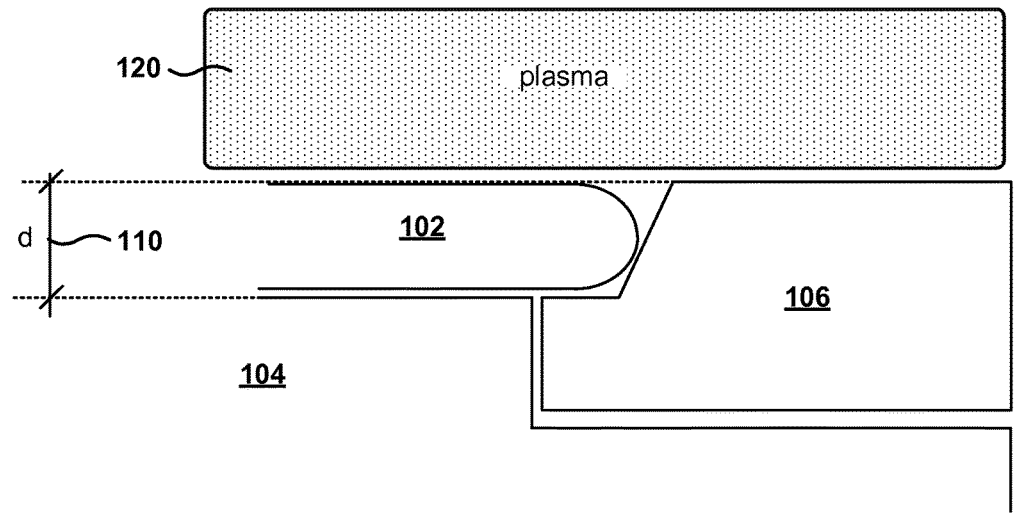
FIG. 2A is a detailed side view of an edge portion of the wafer, according to one embodiment.

FIG. 2A is a detailed side view of an edge portion of the wafer, according to one embodiment. Edge ring 106 surrounds the chuck 104. In one embodiment, a portion of the surface of the edge ring 106 extends under the edge of the substrate 102, but in other embodiments, the edge ring 106 may sit next to the substrate 102 without supporting substrate 102. Because substrate 102 is supported by the chuck 104, the RF power is driven through the chuck and into the wafer.

During the etch process, etch byproducts deposit on the inner surfaces of the chamber 114. The etch byproducts can include polymeric residue, titanium and other metallic compounds and silicon compounds. The etch byproducts may deposit on any surface within the chamber 114 where the plasma 120 disassociated process gas species may diffuse to, including edge ring 106 and other inner surfaces of plasma process chamber. Additionally, over time some of the parts of the chamber may be eroded (e.g., reducing the thickness of the edge ring 106) due to the etch process.

FIG. 2A shows how during operation the top surface of edge ring 106 and the top surface of substrate 102 are substantially coplanar. Therefore, the plasma is in contact with a uniform surface at the bottom of the chamber that covers the substrate and the edge ring. Because there is continuity on the surface, the plasma is uniform over the complete surface of the substrate, resulting in uniform processing of the substrate.

Figure 2B:
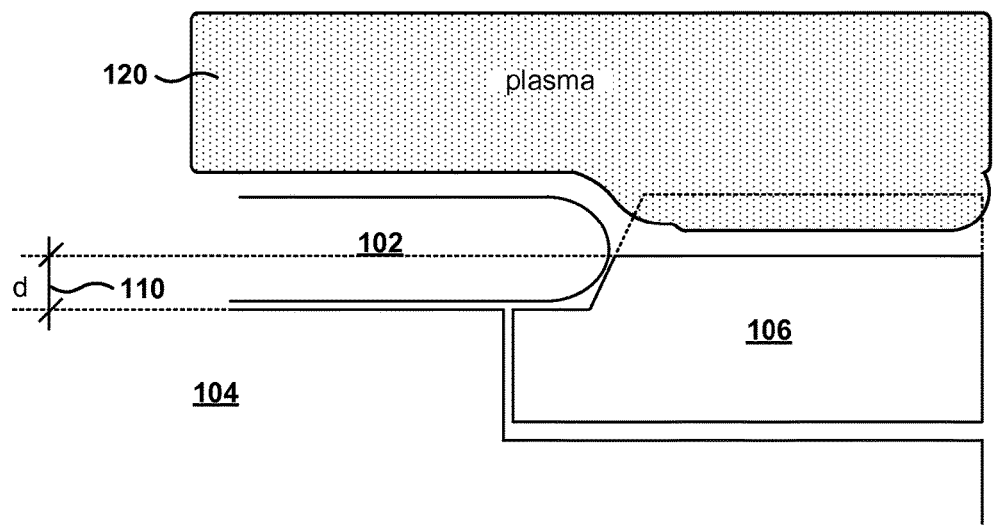
FIG. 2B illustrates the lack of plasma uniformity over the wafer due to the erosion of the edge-ring top surface, according to one embodiment.

FIG. 2B illustrates the lack of plasma uniformity over the wafer due to the erosion of the edge-ring top surface, according to one embodiment. In some chambers, there are a few critical components that determine the amount of time that the chamber can be operated before the chamber has to be opened and the wearable parts replaced. One of those critical components is the edge ring 106. For example, some guidelines indicate that, typically, after the chamber is an operation for 300 hours, the edge ring wears out and has to be replaced. Sometimes, chambers are operated in a mix of different products, different types of etching processes, etc., which may affect how long the consumable part will last before the consumable part has to be replaced. Some administrators set a number of hours of operation of the chamber before the consumable part is replaced, independently of whether the consumable part has actually being worn out or not.

FIG. 2B shows an edge ring 106 that has been in operation for a long period of time. The top surface of the edge ring 106 is lower than in the scenario illustrated in FIG. 2A. In FIG. 2B, the distance d 110 between the top surface of the edge ring 106 and the top surface of the chuck has decreased to about half because of the wear on the top surface of the edge ring.

Now, the top surface of the substrate 102 and the top surface of the edge ring are not coplanar. Therefore, the bottom surface of the chamber where the plasma is produced is not uniform, resulting in lack of uniformity over the surface of the wafer, particularly at the edge of the wafer where the plasma discontinuity occurs. Consequently, the edge of the wafer is not processed correctly and all or part of the wafer will not be processed according to spec.

Rather than conservatively setting a number of hours of operation of the chamber before replacing the part, often based on the worst case scenario, it is beneficial to measure the wear (i.e., erosion rate) on the part of interest and only open the chamber when it is absolutely necessary. Opening the chamber for cleaning is an expensive operation because it means downtime on the semiconductor manufacturing equipment, and because the chamber has to go through a complete cleaning (e.g., wet clean). Further, the chamber may have to be requalified, a process that could take up one or two days in which the machine cannot be operated. If the time that the machine can be operated between cleanups could be extended, this would result in significant performance improvements and better return on investment for the semiconductor manufacturing equipment.

Figure 2C:
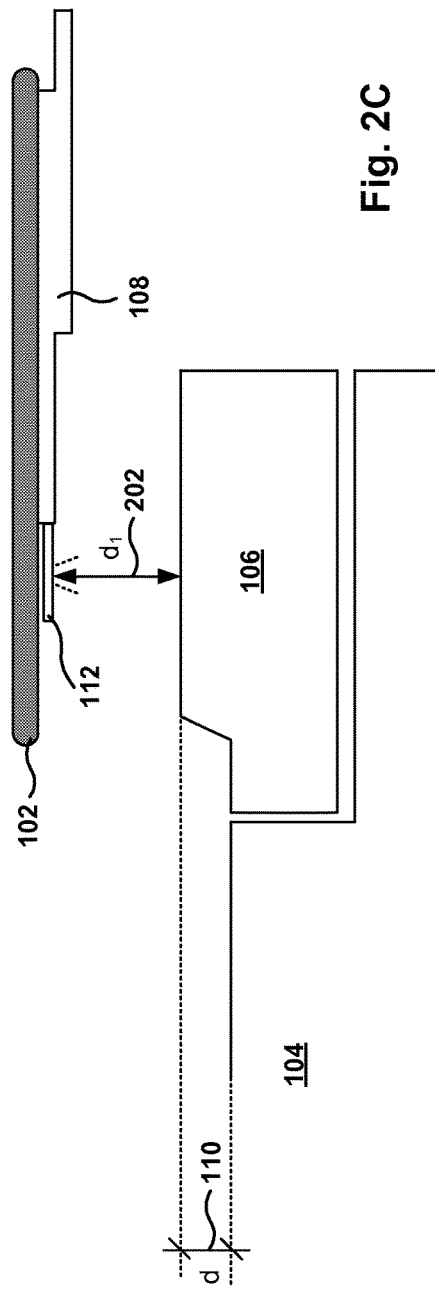
FIG. 2C illustrates the measurement of the distance from the distance sensor to the edge ring when loading the wafer, according to one embodiment.

FIG. 2C illustrates the measurement of the distance from the distance sensor to the edge ring when loading the wafer, according to one embodiment. In one embodiment, a distance sensor 112, also referred to herein as distance measurement probe, is mounted on the transfer arm 108. As the transfer arm 108 moves in and out of the chamber, the distance from the distance sensor to the chamber part, or parts, is measured and correlated to the position of the probe to generate a surface profile of the measured part.

By monitoring the surface profile, the wear rate of consumable parts can be determined in near real time. In one embodiment, the distance sensor is an optical distance measurement device, such as a confocal chromatic measurement system or a low-coherence interferometry device. These devices are small enough and have the resolution required to detect the change of interest, can be operated in a vacuum, and can measure the distance to electrical and non-electrical conductors. In another embodiment, capacitance distance measurement probes may be suitable for some applications to measure wear on metal parts or dielectric materials installed over metal parts.

As an example of a distance sensor, with confocal measurement, a polychromatic white light is focused onto a target surface by a multi-lens optical system. The lenses are arranged so that the white light is dispersed into a monochromatic light by controlled chromatic aberration. A specific distance to the target is assigned to each wavelength by a factory calibration. The light reflected from the target surface is passed through a confocal aperture onto a spectrometer which detects and processes the spectral changes.

As the transfer arm 108 enters the chamber, the transfer arm 108 passes very close to the edge ring, right above the edge ring. In one embodiment, as the distance sensor 202 passes over edge ring 106, one or more measurements are taken of the distance $d_1$ 202 between the distance sensor 112 and the top surface of the edge ring 106.

In one embodiment, the controller knows the exact position of the transfer arm 108, so by tracking distance $d_1$ 202 over time, it is possible to identify the changes on the location of the top surface of the edge ring 106. This way, the wear of the edge ring 106 can be estimated.

In one embodiment, the distance $d_1$ is measured when the edge ring is first placed in the chamber. Afterwards, the distance $d_1$ is measured periodically and compared to the original $d_1$. When the difference between the first $d_1$ and the current measurement of $d_1$ is above a predefined threshold $t_1$, then it is time to change the edge ring. Therefore, a clear picture is available on how much the edge ring is wearing out by identifying the changes in $d_1$ 202.

In one embodiment, the distance measurement is taken while the transfer arm is moving over the edge ring, but in another embodiment, the transfer arm is stopped above the edge ring and the distance measurement is taken while the transfer arm is resting.

It is noted that one of the limitations for the distance sensor chosen is that the distance sensor, when loaded on the transfer arm, must fit through the slot where the wafer enters the chamber, and the distance sensor must be able to avoid hitting or damaging any of the components within the chamber.

Figure 2D:
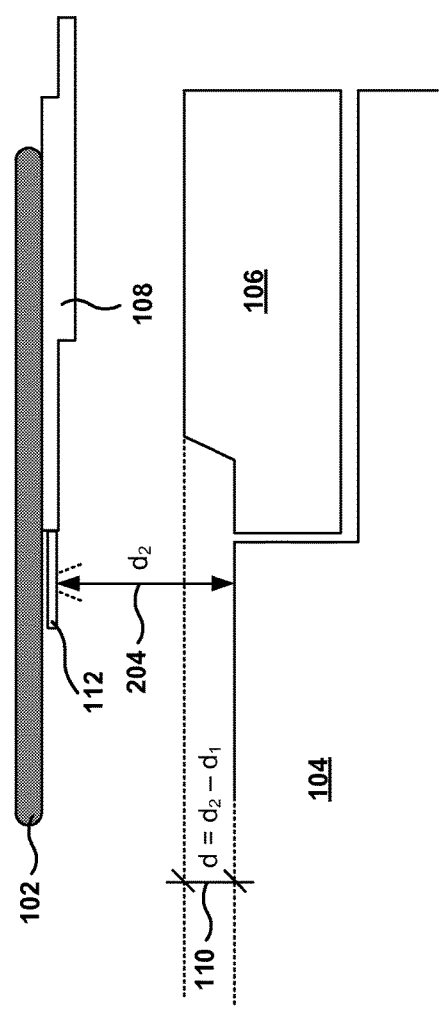
FIG. 2D illustrates the measurement of the distance from the distance sensor to the top surface of the chuck when loading the wafer, according to one embodiment.

FIG. 2D illustrates the measurement of the distance from the distance sensor to the top surface of the chuck when loading the wafer, according to one embodiment. In one embodiment, the distance sensor 112 takes a second measurement for the distance $d_2$ 204 from the distance sensor 112 to the top surface of the chuck. Then, the vertical distance d between the top plane of the edge ring 106 and the top surface of the chuck is calculated as $d_2-d_1$. The top surface of the chuck 104 does not significantly change over time because, while the chambers in operation, the substrate covers the chuck 104.

In one embodiment, to measure the wear of the edge ring 106, the vertical distance d between the top surface of the edge ring and the top surface of the chuck is monitored over time. Since the chuck doesn't change, the chuck may be used as a point of reference to measure the changes in the edge ring 106. By using the chuck as a reference, variations in the measurement of the distance to the edge ring due to the motion of the transfer arm are minimized.

In another embodiment, the distance d is measured when the edge ring is first placed in the chamber. The distance d is measured periodically and compared to the original d. When the difference between the first d and the current measurement of d is above a predefined threshold $t_2$, then it is time to change the edge ring. Therefore, a clear picture is available on how much the edge ring is wearing out by identifying the changes in distance d 110.

In one embodiment, the distance between the transfer arm and the top of the edge ring may be in the range from 2 to 5 mm, but other values are also possible. In another embodiment, the top window of the chamber also suffers wear over time and the same principle may be applied to measure the wear by having a distance sensor that measures the distance to the top of the chamber. The distance from the top window to the transfer arm may be in the range from 5 to 6 inches, although other values are also possible. Therefore, a distance sensor has to be chosen that can measure distance accurately within this range.

Further, it is noted that the embodiments presented include taking distance measurements while the substrate is loaded on the transfer arm, but it is also possible to take measurements without the substrate mounted on the transfer arm. This way, the substrate does not get in the way of measuring the distance to the top of the chamber if the distance sensor is below the position where the substrate is loaded.

Figure 3:
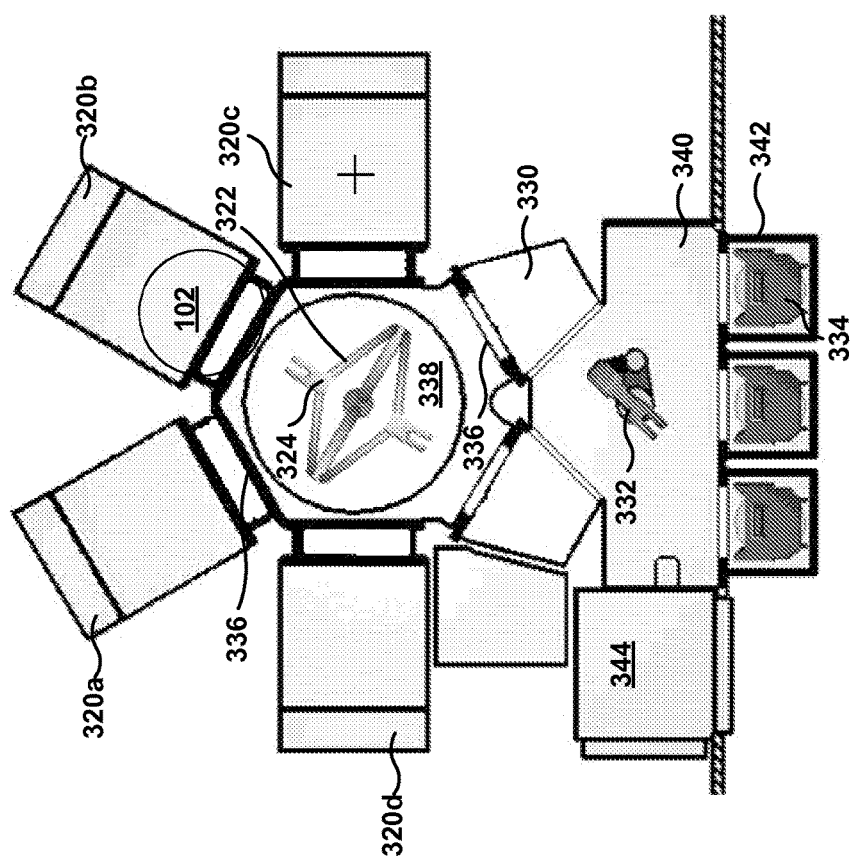
FIG. 3 depicts a typical semiconductor process cluster architecture illustrating the various modules that interface with a vacuum transfer module (VTM).

FIG. 3 depicts a typical semiconductor process cluster architecture illustrating the various modules that interface with a vacuum transfer module (VTM). The arrangement of transfer modules to "transfer" wafers among multiple storage facilities and processing modules is frequently referred to as a "cluster tool architecture" system. Airlock 330, also called a loadlock or a transfer module, is shown in VTM 338 with four processing modules 320a-320d which may be individually optimized to perform various fabrication processes. By way of example, processing modules 320a, 320b, 320c, 320d may be implemented to perform transformer coupled plasma (TCP) substrate etching, layer depositions, and/or sputtering. When speaking in general about airlock 330 or process module 320a, the term station is used at times to refer to either an airlock or a process module. Each station has a facet 336 that interfaces the station to VTM 338. Inside each facet, sensors are used to detect the passing of substrate 102 when going in and out of the respective stations.

Robot 322 transfers substrate 102 between stations. In one embodiment, robot 322 has one arm, and in another embodiment robot 322 has two arms, where each arm has an end-effector 324 to pick the wafers for transport. Front-end robot 332, in atmospheric transfer module 340 (ATM), is used to transfer wafers from cassette, or Front Opening Unified Pod (FOUP) 334 in Load Port Module (LPM) 342 to airlock 330. Aligner 344 in ATM 340 is used to align wafers.

It should be noted that the computer controlling the wafer movement can be local to the cluster architecture, or can be located somewhere in the manufacturing floor, or in a remote location, and connected to the cluster architecture via a network.

Figure 4A:
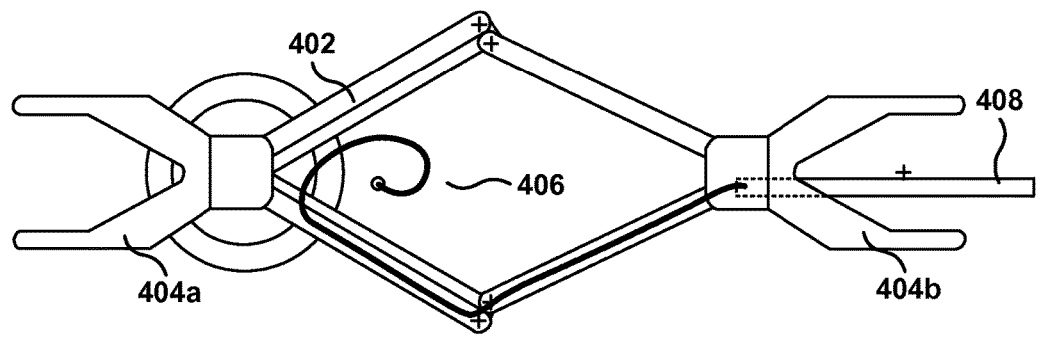
FIG. 4A illustrates a transfer arm with two end effectors and a distance sensor, according to one embodiment.

FIG. 4A illustrates a transfer arm with two end effectors and a distance sensor, according to one embodiment. In one embodiment, a transfer arm 402 with two end effectors 404a, 404b, includes a distance sensor 408 coupled to one of the end effectors. In one embodiment, the distance sensor is a profilometer placed underneath the end effector, which means that when the wafer is loaded, the distance sensor 408 will be situated under the wafer.

In another embodiment, the distance sensor is a confocal chromatic system that changes the focal depth of light on a surface and checks the amount of reflected light. In another embodiment, the distance sensor is a camera, which can be placed directly pointing towards the surface below, and that measures the amount of light reflected from a light source in the distance sensor. In another embodiment, the camera may be placed at an angle and the amount of light reflected changes based on the distance to the surface that reflects the light from the sensor.

The distance sensor 408 is connected via a wire 406 to the controller, where the wire 406 includes power for the distance sensor, as well as a data connection to transfer data.

In one embodiment, one of the stations of the VTM may be used to store the sensor. When a measurement is desired, the transfer arm loads the sensor from the station and then proceeds to enter the chamber with the sensor to perform the measurement. In another embodiment, the distance sensor is mounted permanently on the end effector and it is possible to take a measurement every time a wafer is loaded or unloaded from the chamber.

Figure 4B:
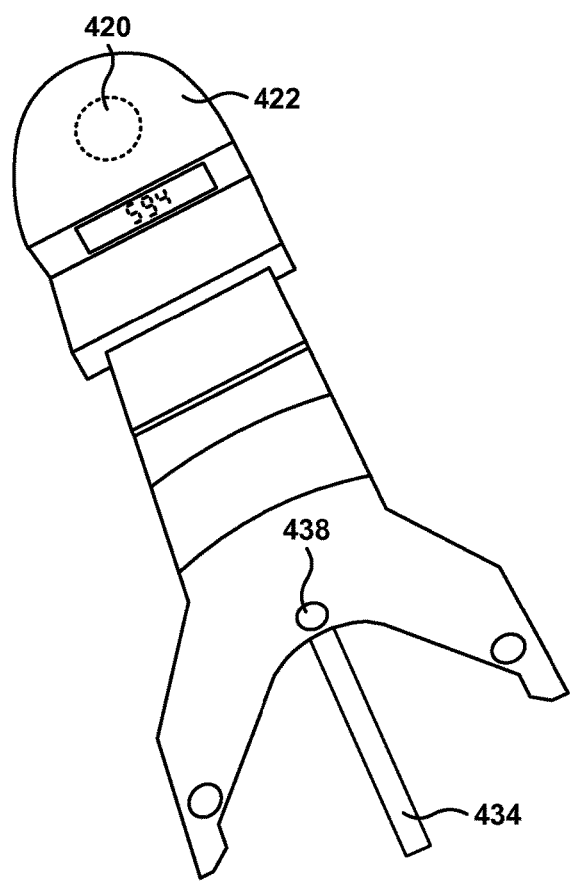
FIG. 4B illustrates a transfer arm with a single end effector and a distance sensor, according to one embodiment.

FIG. 4B illustrates a transfer arm with a single end effector and a distance sensor, according to one embodiment. Robot arm 422 includes a pivot point 420 connected to a robot structure that allows the robot arm 422 to pivot around pivot point 420. In one embodiment, one or more vacuum sensors 438 identify when the wafer is properly loaded on the end effector using the suction effect on the vacuum sensor.

The distance sensor 434 is placed permanently under the end effector, which means that when the substrate is loaded, distance sensor 434 is located underneath the substrate. When the transfer arm enters the chamber, the distance sensor 434 travels over the edge ring and over the chuck, as previously discussed, and distance measurements may be taken to the top surface of the edge ring, and/or to the top surface of the chuck.

In other embodiments, the distance sensor may be situated in other places underneath the end effector. For example, the distance sensor 434 may be situated on the right or on the left fingers of the end effector. In another embodiment, the end effector may be situated below vacuum sensors 438, but any other position is possible, as long as the distance sensor fits through the slot to enter into the chamber and doesn't contact any other parts inside the chamber.

In yet another embodiment, the distance sensor may be mounted on the top surface of the end effector, but the wafer is not loaded on the end effector when the distance sensor is above the edge ring, and the end effector is introduced into the chamber to take measurements without the wafer loaded.

Figure 5A:
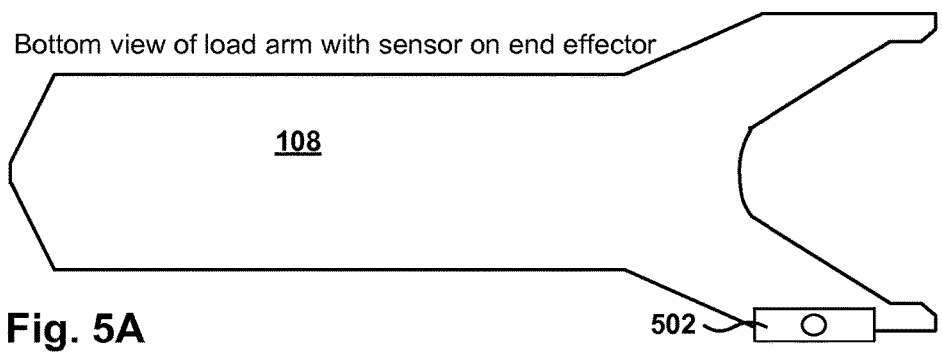
FIG. 5A is a bottom view of the transfer arm with a distance sensor clipped to the end effector, according to one embodiment.

FIG. 5A is a bottom view of the transfer arm 108 with a distance sensor clipped to the end effector, according to one embodiment. In one embodiment, the distance sensor 502 clips to one of the sides of the end effector. In another embodiment (not shown), the distance sensor may be integrated within the end effector itself, and the distance sensor has a low profile in order to maintain, as close as possible, the profile of the end effector to be the same as if the distance sensor were not installed.

In one embodiment, the distance sensor includes a battery, which could be a rechargeable battery, and includes wireless communication capabilities in order to transmit measurement data to the controller. This way, it is not necessary to wire the distance sensor to transmit the information or to power the distance sensor.

In another embodiment, the erosion or wear on the walls of the chamber is measured by measuring the color change in the walls of the chamber. The deposition film may be very thin, so measuring the thickness of the deposition film accurately may be difficult. However, by measuring the color change of the walls, it may be possible to determine when the walls need to be replaced or cleaned.

Figure 5B:
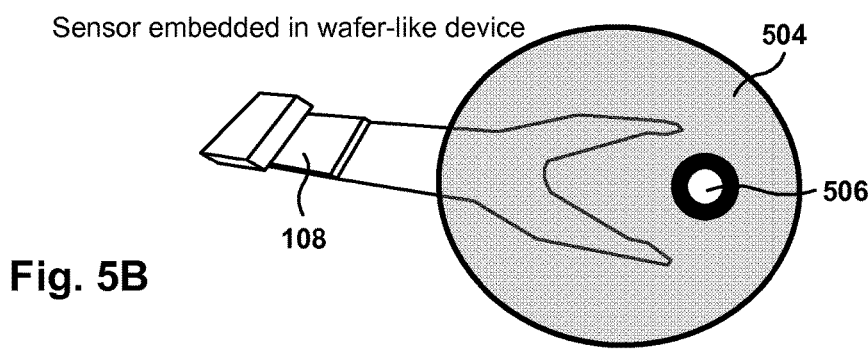
FIG. 5B illustrates a wafer-like device with an embedded distance sensor, according to one embodiment.

FIG. 5B illustrates a wafer-like device with an embedded distance sensor, according to one embodiment. In one embodiment, the distance sensor 506 is mounted on a structure that appears like a wafer to the end effector, i.e., the distance sensor 506 is embedded in the wafer-like structure 504. This way, an existing transfer arm 108 does not have to be modified in order to perform distance measurements.

Every time a measurement is to take place, the end effector loads the wafer-like structure 504 and introduces it into the chamber. It is not necessary to load the structure on the chuck, so after one or more measurements are taken, the transfer arm exits the chamber and unloads the wafer-like structure.

In one embodiment, the wafer-like structure is stored in a buffer within a wafer station, and the end effector loads it from the buffer. In another embodiment, the wafer-like structure could be stored in one of the slots in the transfer airlock.

Figure 6:
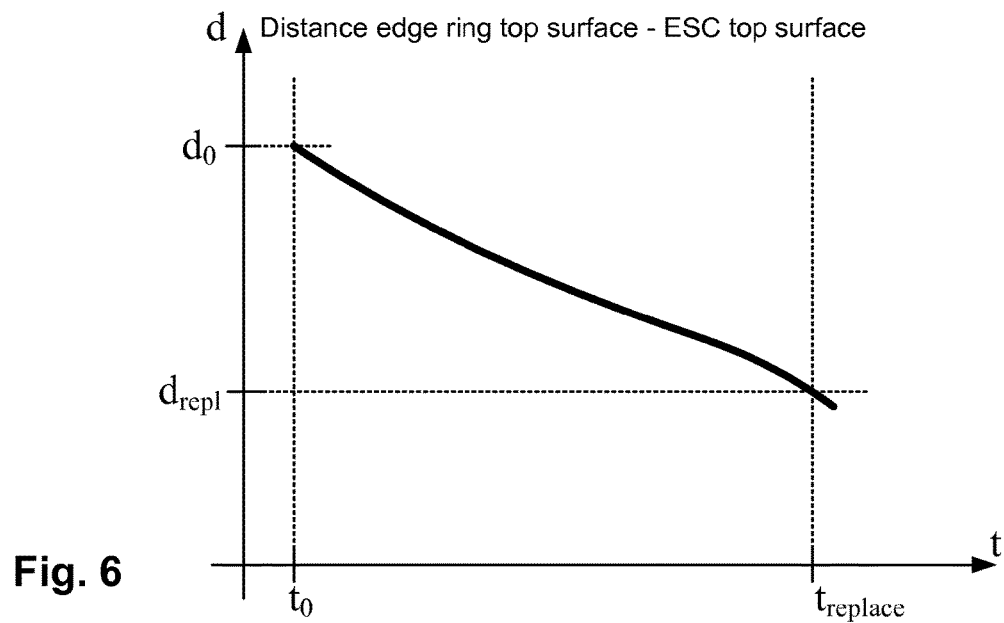
FIG. 6 illustrates the change over time of the vertical distance between the top surface of the edge ring and the chuck, according to one embodiment.

FIG. 6 illustrates the change over time of the vertical distance between the top surface of the edge ring and the chuck, according to one embodiment. It is noted, that when only the distance to the edge ring is measured, the chart looks similar as the one in FIG. 6, but instead of measuring a relative distance between the chuck and the edge ring, the chart would show the distance between the distance sensor and the edge ring.

Initially, after a new edge ring is placed in the chamber, the first measurement of the vertical distance $d_0$ is taking at time $t_0$. Afterwards, measurements are taken regularly to check for the value of the distance d. As the chamber accumulates hours of operation, the edge ring will continue eroding on the top surface due to the exposure to the plasma in the chamber. Therefore, the distance d will gradually decrease. In one embodiment, the edge ring has a width of 3 to 4 mm, but other values are also possible.

When distance d reaches a predetermined threshold $d_{repl}$, then it is time to change the edge ring before the operation of the chamber is affected by non-uniformity at the edge of the wafer. The rate of erosion may or may not be linear, depending on the different processes performed inside the chamber, as some processes will erode the edge ring faster than other processes.

As discussed earlier, the edge ring wears out over time, but the chuck doesn't, so the change in the distance d, which measures the vertical distance between the top surface of the edge ring and the top surface of the chuck, is attributed to the erosion on the edge ring.

The same principles presented above may also be utilized to measure deposition on a consumable part. However, the process is reversed, in that over time, the distance from the top of the edge ring to the top of the chuck will increase due to the deposition on the edge ring. A threshold accumulation is defined, which translates to a threshold distance, and when d becomes greater than the threshold distance, then it is time to replace or clean the edge ring due to the excessive deposition on the edge ring.

Figure 7:
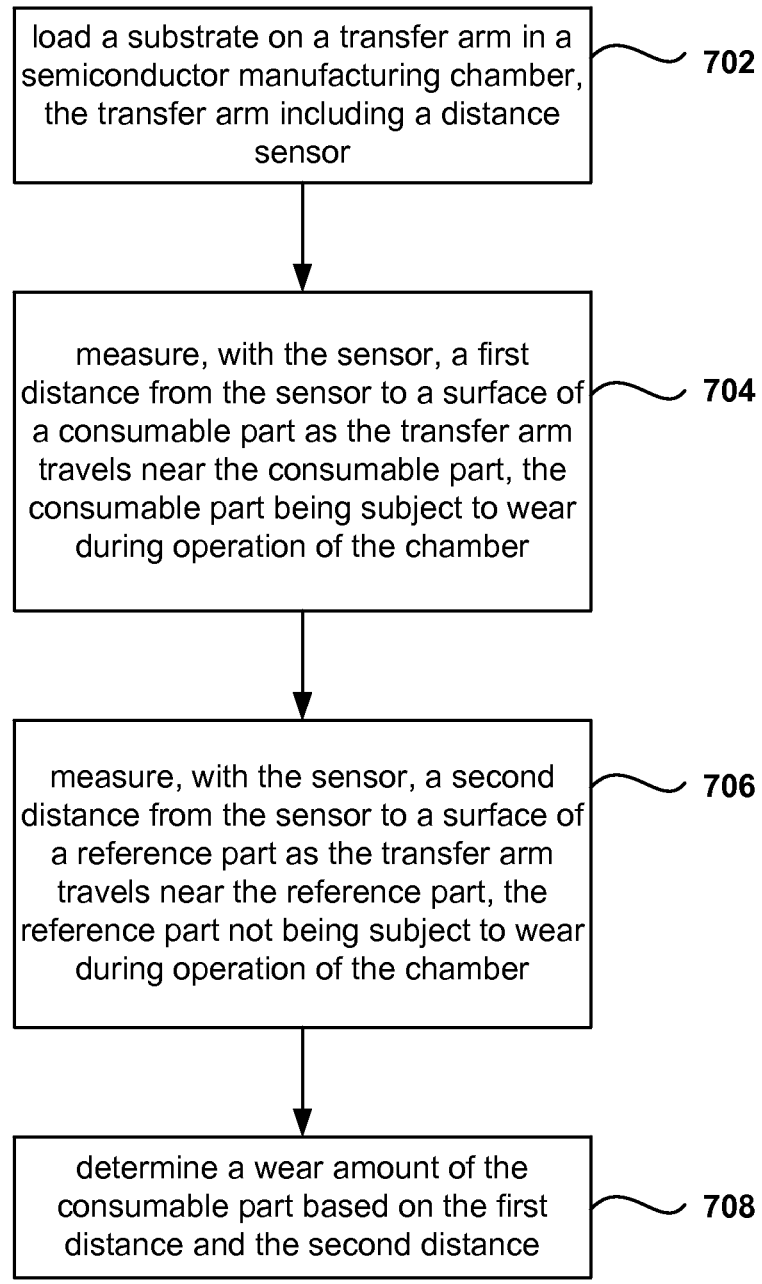
FIG. 7 is a flowchart of a method for determining wear of a consumable part in a semiconductor processing apparatus, according to one embodiment.

FIG. 7 is a flowchart of a method for determining wear of a consumable part in a semiconductor processing apparatus, according to one embodiment. While the various operations in this flowchart are presented and described sequentially, one of ordinary skill will appreciate that some or all of the operations may be executed in a different order, be combined or omitted, or be executed in parallel.

As discussed above, embodiments perform in-situ measurement of consumable parts wear with near real-time feedback. This method offers advantages over typical methods employed that merely predict end of life based on time, or by observing process shift in a later wafer inspection step. In-situ, real-time measurement can be used to predict consumable part lifetime for predictable maintenance. It can potentially be used with a feedback algorithm to make process adjustments based on part wear to improve wafer to wafer repeatability, increase part lifetime, and increase system availability for production.

In operation 702, a substrate is loaded on a transfer arm in a semiconductor manufacturing chamber, where the transfer arm includes a distance sensor. From operation 702, the method flows to operation 704 for measuring, with the distance sensor, a first distance from the distance sensor to a surface of a consumable part as the transfer arm travels near the consumable part. The consumable part is subject to wear during operation of the chamber.

From operation 704, the method flows to operation 706 for measuring, with the distance sensor, a second distance from the distance sensor to a surface of a reference part as the transfer arm travels near the reference part, the reference part not being subject to wear during operation of the chamber.

From operation 706, the method flows to operation 708, where a wear amount of the consumable part is determined based on the first distance and the second distance. In one embodiment, the wear is determined based on the difference between the second distance and the first distance, which is the vertical distance between a top surface of the consumable part and a top surface of the reference part. This distance between the top surfaces is monitored over time in order to determine when the consumable part is worn off and needs replacement. In one embodiment, the consumable part is an edge ring and the reference part is a chuck configured to hold the substrate during processing.

Figure 8:
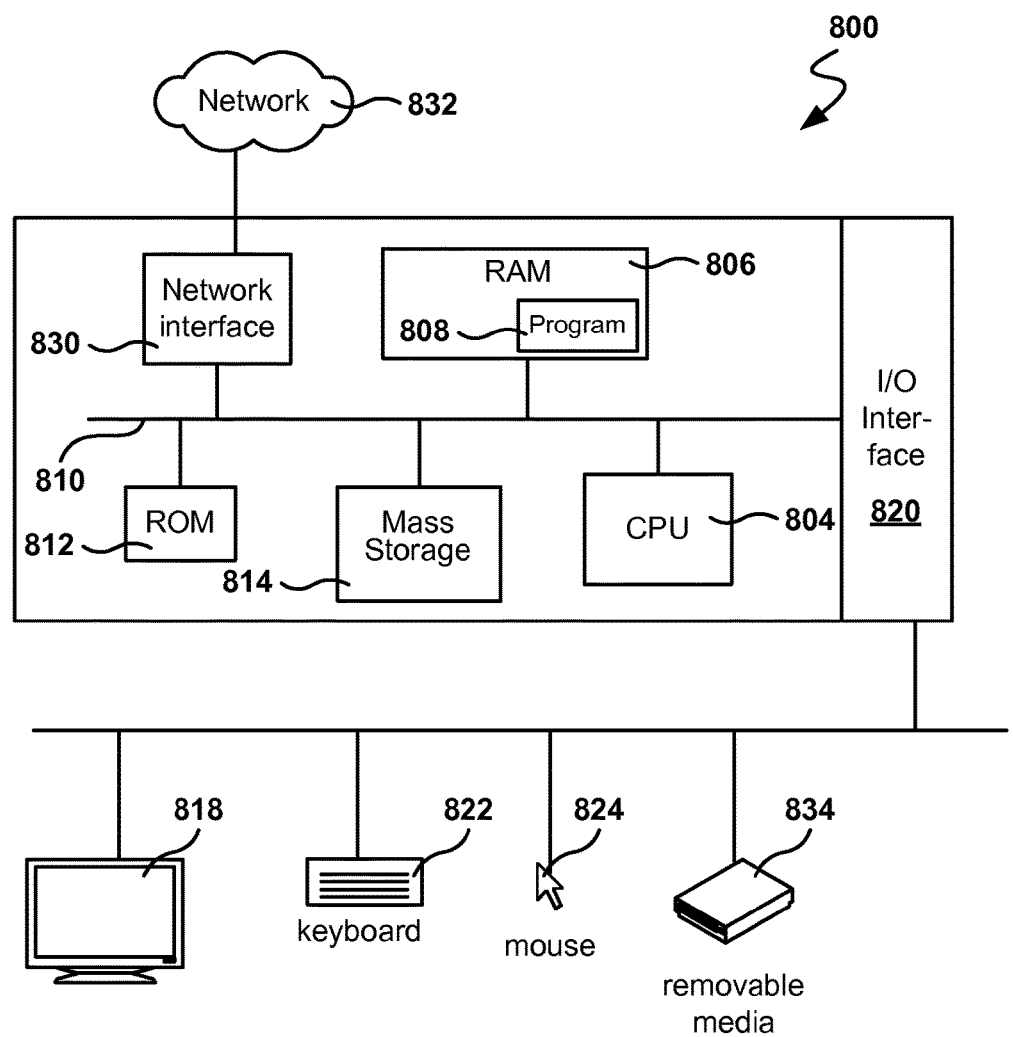
FIG. 8 is a simplified schematic diagram of a computer system for implementing embodiments of the present disclosure.

FIG. 8 is a simplified schematic diagram of a computer system 800 for implementing embodiments of the present disclosure. It should be appreciated that the methods described herein may be performed with a digital processing system, such as a conventional, general-purpose computer system. Special purpose computers, which are designed or programmed to perform only one function may be used in the alternative. The computer system includes a central processing unit (CPU) 804, which is coupled through bus 810 to random access memory (RAM) 806, read-only memory (ROM) 812, and mass storage device 814. System controller program 808 resides in RAM 806, but can also reside in mass storage device 814.

Mass storage device 814 represents a persistent data storage device such as a floppy disc drive or a fixed disc drive, which may be local or remote. Network interface 830 provides connections via network 832, allowing communications with other devices. It should be appreciated that CPU 804 may be embodied in a general-purpose processor, a special purpose processor, or a specially programmed logic device. Input/Output (I/O) interface provides communication with different peripherals and is connected with CPU 804, RAM 806, ROM 812, and mass storage device 814, through bus 810. Sample peripherals include display 818, keyboard 822, cursor control 824, removable media device 834, etc.

Display 818 is configured to display the user interfaces described herein. Keyboard 822, cursor control 824, removable media device 834, and other peripherals are coupled to I/O interface 820 in order to communicate information in command selections to CPU 804. It should be appreciated that data to and from external devices may be communicated through I/O interface 820. The embodiments can also be practiced in distributed computing environments where tasks are performed by remote processing devices that are linked through a wire-based or wireless network.

Embodiments may be practiced with various computer system configurations including hand-held devices, microprocessor systems, microprocessor-based or programmable consumer electronics, minicomputers, mainframe computers and the like. The embodiments can also be practiced in distributed computing environments where tasks are performed by remote processing devices that are linked through a network.

With the above embodiments in mind, it should be understood that the embodiments can employ various computer-implemented operations involving data stored in computer systems. These operations are those requiring physical manipulation of physical quantities. Any of the operations described herein that form part of the embodiments are useful machine operations. The embodiments also relates to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data may be processed by other computers on the network, e.g., a cloud of computing resources.

One or more embodiments can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they can occur at slightly different times, or may be distributed in a system which allows the occurrence of the processing operations at various intervals associated with the processing, as long as the processing of the overlay operations are performed in the desired way.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the embodiments are not to be limited to the details given herein, but may be modified within the scope and equivalents of the appended claims.

What is claimed is:

1. A chamber for processing a substrate, the chamber comprising:
    a reference part in the chamber, the reference part not being subject to wear during operation of the chamber;
    a consumable part within the chamber, the consumable part being subject to wear during operation of the chamber;
    a transfer arm for transferring the substrate into the chamber;
    a sensor on the transfer arm, wherein the sensor is configured to measure a first distance from the sensor to a surface of the consumable part as the transfer arm travels over the consumable part along a linear travel position into the chamber, wherein the sensor is configured to measure a second distance from the sensor to a surface of the reference part as the transfer arm travels along the linear travel position over the reference part; and a controller configured to determine a wear amount of the consumable part based on the first distance and the second distance.

2. The chamber as recited in claim 1, wherein the controller calculates a distance difference between a plane of the surface of the consumable part and a plane of the surface of the reference part, the distance difference being equal to the first distance minus the second distance.

3. The chamber as recited in claim 2, wherein the controller tracks a change of the distance difference over time starting when the consumable part is first installed.

4. The chamber as recited in claim 3, wherein the controller determines that the consumable part is to be replaced when the distance difference changes by a predetermined amount in reference to the distance difference measured when the consumable part was first installed.

5. The chamber as recited in claim 1, wherein the wear amount on the consumable part is determined without having to open the chamber, wherein the sensor is a non-contact distance measurement device.

6. The chamber as recited in claim 1, wherein the controller calculates a distance difference between a plane of the surface of the consumable part and a plane of the surface of the reference part, the distance difference being equal to the first distance minus the second distance, wherein the controller determines a process parameter change to compensate for wear of the consumable part based on the change of the distance difference over time starting when the consumable part is first installed.

7. The chamber as recited in claim 1, wherein the sensor is coupled to an end effector of the transfer arm.

8. The chamber as recited in claim 1, wherein the sensor is one of a depth camera, or a confocal chromatic measurement device, or a low coherence interferometry measurement device, or a capacitance distance sensor, or a color change detector.

9. The chamber as recited in claim 1, further including:
a station of a vacuum transfer chamber or a load lock for storing the sensor, wherein the transfer arm loads the sensor from the station in the vacuum transfer chamber or load lock.

10. The chamber as recited in claim 1, wherein the consumable part is an edge ring, wherein the reference part is a chuck for holding the substrate during operation of the chamber.

11. The chamber as recited in claim 1, wherein the sensor is connected wirelessly to the controller, wherein the sensor includes a battery.

12. The chamber as recited in claim 1, wherein the sensor is mountable on an end effector of the transfer arm.

13. The chamber as recited in claim 1, wherein the sensor is mounted on a structure similar to a substrate such that the transfer arm loads the sensor as if the transfer arm were loading a substrate.

14. A method for determining wear of a consumable part, the method comprising:
loading a substrate on a transfer arm in a semiconductor manufacturing chamber, the transfer arm including a sensor;
measuring, with the sensor, a first distance from the sensor to a surface of a consumable part as the transfer arm travels over the consumable part along a linear travel position into the semiconductor manufacturing chamber, the consumable part being subject to wear during operation of the chamber;
measuring, with the sensor, a second distance from the sensor to a surface of a reference part as the transfer arm travels over the reference part along the linear travel position, the reference part not being subject to wear during operation of the chamber; and
determining a wear amount of the consumable part based on the first distance and the second distance.

15. The method as recited in claim 14, wherein determining the wear amount further includes:
calculating a distance difference between a plane of the surface of the consumable part and a plane of the surface of the reference part, the distance difference being equal to the first distance minus the second distance.

16. The method as recited in claim 15, further including:
tracking a change of the distance difference over time starting when the consumable part is first installed, wherein the consumable part is to be replaced when the distance difference changes by a predetermined amount in reference to the distance difference measured when the consumable part was first installed.

17. The method as recited in claim 14, wherein the wear amount on the consumable part is determined without having to open the chamber, wherein the sensor is a non-contact distance measurement device.

18. The method as recited in claim 14, wherein the sensor is one of a depth camera, or a confocal chromatic measurement device, or a low coherence interferometry measurement device, or a capacitance distance sensor, or a color change detector.

19. A chamber for processing a substrate, the chamber comprising:
a reference part in the chamber;
a consumable part within the chamber, the consumable part accumulating deposition during operation of the chamber;
a transfer arm for transferring the substrate into the chamber;
a sensor on the transfer arm, wherein the sensor is configured to measure a first distance from the sensor to a surface of the consumable part as the transfer arm travels over the consumable part along a linear travel position into the chamber, wherein the sensor is configured to measure a second distance from the sensor to a surface of the reference part as the transfer arm travels over the reference part along the linear travel position; and
a controller configured to determine an amount of deposition on the consumable part based on the first distance and the second distance.

20. The chamber as recited in claim 19, wherein the controller calculates a distance difference between a plane of the surface of the consumable part and a plane of the surface of the reference part, the distance difference being equal to the first distance minus the second distance;
wherein the controller tracks a change of the distance difference over time starting when the consumable part is first installed; and
wherein the controller determines that the consumable part is to be replaced when the distance difference changes by a predetermined amount in reference to the distance difference measured when the consumable part was first installed.

* * * * *